(12) United States Patent
Sudo

(10) Patent No.: US 7,517,920 B2
(45) Date of Patent: Apr. 14, 2009

(54) DENTURE FIXATIVE COMPOSITION

(75) Inventor: Akihiro Sudo, Palatine, IL (US)

(73) Assignee: Sunstar Inc., Takatsuki-shi (JP)

( * ) Notice: Subject to any disclaimer, the term of this patent is extended or adjusted under 35 U.S.C. 154(b) by 78 days.

(21) Appl. No.: 11/643,514

(22) Filed: Dec. 21, 2006

(65) Prior Publication Data

US 2007/0149643 A1    Jun. 28, 2007

Related U.S. Application Data

(63) Continuation-in-part of application No. 11/319,916, filed on Dec. 28, 2005, now abandoned.

(51) Int. Cl.
*A61K 6/08* (2006.01)
(52) U.S. Cl. .................. 523/120; 524/35; 524/43; 524/45; 433/168.1
(58) Field of Classification Search .............. 523/120; 524/43, 45, 35
See application file for complete search history.

(56) References Cited

U.S. PATENT DOCUMENTS

| | | |
|---|---|---|
| 1,917,902 A | 7/1933 | Rowe |
| 2,047,398 A | 7/1936 | Voss et al. |
| 2,664,631 A | 1/1954 | Hollander et al. |
| 2,866,775 A | 12/1958 | Sellers et al. |
| 2,897,593 A | 8/1959 | Hollander et al. |
| 2,978,812 A | 4/1961 | Rosenthal et al. |
| 2,997,399 A | 8/1961 | Eberhard et al. |
| 3,003,988 A | 10/1961 | Germann et al. |
| 3,531,427 A | 9/1970 | Kervenski et al. |
| 3,575,915 A | 4/1971 | Novak et al. |
| 3,736,274 A | 5/1973 | Schoenholz et al. |
| 3,740,361 A | 6/1973 | Altwirth |
| 3,833,518 A | 9/1974 | Rubin et al. |
| 3,855,052 A | 12/1974 | Mestetsky |
| 3,868,259 A | 2/1975 | Keegan et al. |
| 3,868,260 A | 2/1975 | Keegan et al. |
| 3,868,339 A | 2/1975 | Keegan et al. |
| 3,868,340 A | 2/1975 | Keegan et al. |
| 3,868,432 A | 2/1975 | Keegan et al. |
| 3,873,588 A | 3/1975 | Osawa et al. |
| 3,878,135 A | 4/1975 | Keegan et al. |
| 3,878,138 A | 4/1975 | Keegan et al. |
| 3,919,138 A | 11/1975 | Keegan et al. |
| 3,919,139 A | 11/1975 | Keegan et al. |
| 3,919,357 A | 11/1975 | Keegan et al. |
| 3,926,870 A | 12/1975 | Keegan et al. |
| 3,930,871 A | 1/1976 | Starace |
| 3,936,402 A | 2/1976 | Keegan et al. |
| 3,963,685 A | 6/1976 | Abrahams |
| 3,983,095 A | 9/1976 | Bashaw et al. |
| 3,990,149 A | 11/1976 | Nedwig |
| 4,001,151 A | 1/1977 | Keegan et al. |
| 4,136,163 A | 1/1979 | Watson et al. |
| 4,138,477 A | 2/1979 | Gaffar |
| 4,142,014 A | 2/1979 | Mestetsky |
| 4,183,914 A | 1/1980 | Gaffar et al. |
| 4,202,098 A | 5/1980 | Russo |
| 4,211,681 A | 7/1980 | Braun et al. |
| 4,217,342 A | 8/1980 | Gaffar et al. |
| 4,217,343 A | 8/1980 | Gaffar et al. |
| 4,239,488 A | 12/1980 | Sempler |
| 4,280,936 A | 7/1981 | Dhabhar et al. |
| 4,318,742 A | 3/1982 | Lokken |
| 4,373,036 A | 2/1983 | Chang et al. |
| 4,389,419 A | 6/1983 | Lim et al. |
| 4,393,080 A | 7/1983 | Pawelchak et al. |
| 4,465,517 A | 8/1984 | Shields |
| 4,470,814 A | 9/1984 | Chang et al. |
| 4,474,902 A | 10/1984 | Dhabhar et al. |
| 4,495,314 A | 1/1985 | Keegan |
| 4,503,116 A | 3/1985 | Lapidus |
| 4,514,528 A | 4/1985 | Dhabhar et al. |
| 4,518,721 A | 5/1985 | Dhabhar et al. |
| 4,521,551 A | 6/1985 | Chang et al. |
| 4,522,956 A | 6/1985 | Dhabhar et al. |
| 4,529,748 A | 7/1985 | Wienecke |
| 4,530,942 A | 7/1985 | Dhabhar et al. |
| 4,542,168 A | 9/1985 | Chang et al. |
| 4,569,955 A | 2/1986 | Dhabhar |
| 4,608,088 A | 8/1986 | Lokken |
| 4,632,880 A | 12/1986 | Lapidus |

(Continued)

FOREIGN PATENT DOCUMENTS

EP    0202819 A2    11/1986

(Continued)

OTHER PUBLICATIONS

Handbook for Japanese Pharmacopoeia, 15th Ed., C-3262-C-3265.
Handbook for Japanese Pharmacopoeia, 15th Ed., C-3262-C-3265, Apr. 2006.

*Primary Examiner*—Tae H Yoon
(74) *Attorney, Agent, or Firm*—Drinker Biddle & Reath LLP

(57) ABSTRACT

A denture fixative composition containing lower alkyl vinyl ether-maleic anhydride copolymers, water-insoluble and water-swelling polymers, and at least one additional adhesive material which can be used as a denture fixative paste, liquid, powder, aerosol, dissolving tablet, liner or adhesive-like strip.

21 Claims, 3 Drawing Sheets

U.S. PATENT DOCUMENTS

| | | | |
|---|---|---|---|
| 4,664,630 A | 5/1987 | Lokken | |
| 4,680,319 A | 7/1987 | Gimpel et al. | |
| 4,758,630 A | 7/1988 | Shah et al. | |
| 4,772,470 A | 9/1988 | Inoue et al. | |
| 4,804,412 A | 2/1989 | Komiyama et al. | |
| 4,866,023 A | 9/1989 | Ritter et al. | |
| 4,880,702 A | 11/1989 | Homan et al. | |
| 4,888,238 A | 12/1989 | Katz et al. | |
| 4,894,232 A | 1/1990 | Reül et al. | |
| 4,910,247 A | 3/1990 | Haldar et al. | |
| 4,948,848 A | 8/1990 | Tazi et al. | |
| 4,980,391 A | 12/1990 | Kumar et al. | |
| 5,001,170 A | 3/1991 | Keegan | |
| 5,006,571 A | 4/1991 | Kumar et al. | |
| 5,011,868 A | 4/1991 | Keegan | |
| 5,024,701 A | 6/1991 | Desmarais | |
| 5,037,924 A | 8/1991 | Tazi et al. | |
| 5,049,235 A | 9/1991 | Barcus et al. | |
| 5,066,709 A | 11/1991 | Chaudhuri et al. | |
| 5,073,604 A | 12/1991 | Holeva et al. | |
| 5,082,913 A | 1/1992 | Tazi et al. | |
| 5,093,387 A | 3/1992 | Schobel et al. | |
| 5,106,914 A | 4/1992 | Russell et al. | |
| 5,147,941 A | 9/1992 | Tazi et al. | |
| 5,158,825 A | 10/1992 | Altwirth | |
| 5,166,233 A | 11/1992 | Kuroya et al. | |
| 5,192,362 A | 3/1993 | Harvey et al. | |
| 5,204,414 A | 4/1993 | Pelah et al. | |
| 5,209,777 A | 5/1993 | Altwirth | |
| 5,239,017 A | 8/1993 | Pelesko et al. | |
| 5,286,764 A | 2/1994 | Prosise | |
| 5,288,480 A | 2/1994 | Gaffar et al. | |
| 5,298,534 A | 3/1994 | Prosise et al. | |
| 5,302,628 A | 4/1994 | Lim et al. | |
| 5,304,616 A | 4/1994 | Rajaiah et al. | |
| 5,340,918 A | 8/1994 | Kittrell et al. | |
| 5,362,789 A | 11/1994 | Kwak et al. | |
| 5,369,145 A | 11/1994 | Gasman et al. | |
| 5,395,867 A | 3/1995 | Prosise | |
| 5,424,058 A | 6/1995 | Rajaiah et al. | |
| 5,498,439 A | 3/1996 | Bonner | |
| 5,525,652 A | 6/1996 | Clarke et al. | |
| 5,543,443 A | 8/1996 | Rajaiah et al. | |
| 5,561,177 A | 10/1996 | Khaledi et al. | |
| 5,624,745 A | 4/1997 | Lapidus | |
| 5,635,568 A | 6/1997 | Plochocka et al. | |
| 5,658,586 A | 8/1997 | Rajaiah et al. | |
| 5,696,181 A | 12/1997 | Chang et al. | |
| 5,750,591 A | 5/1998 | Clarke et al. | |
| 5,753,723 A | 5/1998 | Chang et al. | |
| 5,760,102 A | 6/1998 | Hall et al. | |
| 5,763,554 A | 6/1998 | Prosise et al. | |
| 5,830,933 A | 11/1998 | Synodis et al. | |
| 5,872,160 A | 2/1999 | Liang et al. | |
| 5,872,161 A | 2/1999 | Liang et al. | |
| 5,877,233 A | 3/1999 | Liang et al. | |
| 5,879,691 A | 3/1999 | Sagel et al. | |
| 5,880,172 A | 3/1999 | Rajaiah et al. | |
| 5,891,453 A | 4/1999 | Sagel et al. | |
| 5,894,017 A | 4/1999 | Sagel et al. | |
| 5,900,470 A | 5/1999 | Prosise et al. | |
| 5,939,506 A | 8/1999 | Plochocka | |
| 5,959,035 A | 9/1999 | Guo | |
| 5,959,053 A | 9/1999 | Plochocka | |
| 5,987,689 A | 11/1999 | Gordon | |
| 6,025,411 A | 2/2000 | Wong et al. | |
| RE36,657 E | 4/2000 | Synodis et al. | |
| 6,046,291 A | 4/2000 | Zhang et al. | |
| 6,069,188 A | 5/2000 | Rajaiah et al. | |
| 6,110,989 A | 8/2000 | Clarke | |
| 6,124,374 A | 9/2000 | Kolias et al. | |
| 6,166,102 A | 12/2000 | Ahn et al. | |
| 6,184,325 B1 | 2/2001 | Plochocka | |
| 6,197,331 B1 | 3/2001 | Lerner et al. | |
| 6,239,191 B1 | 5/2001 | Wong et al. | |
| 6,276,937 B1 | 8/2001 | Gasman | |
| 6,294,594 B1 | 9/2001 | Borja et al. | |
| 6,350,794 B1 | 2/2002 | Borja | |
| 6,355,706 B1 | 3/2002 | Rajaiah et al. | |
| 6,375,963 B1* | 4/2002 | Repka et al. | 424/402 |
| 6,423,762 B1 | 7/2002 | Wong et al. | |
| 6,475,497 B1 | 11/2002 | Rajaiah et al. | |
| 6,475,498 B1 | 11/2002 | Rajaiah et al. | |
| 6,500,406 B1 | 12/2002 | Rajaiah et al. | |
| 6,503,312 B2 | 1/2003 | Altwirth | |
| 6,518,227 B2 | 2/2003 | Woosley | |
| 6,593,396 B2 | 7/2003 | Muramatsu et al. | |
| 6,617,374 B1 | 9/2003 | Rajaiah et al. | |
| 6,638,881 B2 | 10/2003 | Lapidus | |
| 6,677,391 B1 | 1/2004 | Rajaiah et al. | |
| 6,682,722 B2 | 1/2004 | Majeti et al. | |
| 6,696,058 B2 | 2/2004 | Pellico et al. | |
| 6,706,781 B2 | 3/2004 | Rajaiah et al. | |
| 6,764,987 B1 | 7/2004 | Gaur | |
| 6,837,711 B1 | 1/2005 | Yordinsky | |
| 6,854,973 B2 | 2/2005 | Butcher et al. | |
| 2002/0013384 A1 | 1/2002 | Muramatsu et al. | |
| 2002/0111394 A1 | 8/2002 | Prosise et al. | |
| 2003/0027887 A1 | 2/2003 | Rajaiah et al. | |
| 2003/0108488 A1 | 6/2003 | Rajaiah et al. | |
| 2003/0108489 A1 | 6/2003 | Rajaiah et al. | |
| 2003/0143214 A1 | 7/2003 | Pellico et al. | |
| 2004/0028930 A1 | 2/2004 | Wong et al. | |
| 2004/0034120 A1 | 2/2004 | Patel et al. | |
| 2004/0048948 A1 | 3/2004 | Yamashita et al. | |
| 2004/0091838 A1 | 5/2004 | Loertscher | |
| 2004/0166068 A1 | 8/2004 | Rajaiah et al. | |
| 2005/0031552 A1* | 2/2005 | Mori et al. | 424/53 |
| 2005/0032940 A1 | 2/2005 | Muramatsu et al. | |
| 2005/0054583 A1 | 3/2005 | Wang et al. | |
| 2005/0191599 A1 | 9/2005 | Slack et al. | |
| 2005/0192376 A1 | 9/2005 | Ha et al. | |
| 2005/0228066 A1 | 10/2005 | Wong et al. | |
| 2006/0025494 A1 | 2/2006 | Gasman | |
| 2007/0149642 A1* | 6/2007 | Sudo | 523/120 |

FOREIGN PATENT DOCUMENTS

| | | |
|---|---|---|
| EP | 1396252 A1 | 3/2004 |
| EP | 0812179 B1 | 4/2004 |
| EP | 1508329 A1 | 2/2005 |
| EP | 1235544 B1 | 7/2005 |
| EP | 0774949 B1 | 10/2005 |
| JP | 8511449 | 12/1996 |
| JP | 10506928 | 7/1998 |
| JP | 11511365 | 10/1999 |
| JP | 2002502429 | 1/2002 |
| JP | 2002505604 | 2/2002 |
| JP | 2002516343 | 6/2002 |
| JP | 2002525300 | 8/2002 |
| JP | 2002529489 | 9/2002 |
| JP | 2002531475 | 9/2002 |
| JP | 2002532150 | 10/2002 |
| JP | 2003519642 | 6/2003 |
| JP | 2004510542 | 4/2004 |
| WO | WO 99/18140 A1 | 4/1999 |
| WO | WO 00/35410 A1 | 6/2000 |
| WO | WO 2004/058195 A1 | 7/2004 |
| WO | WO 2004/073661 A1 | 9/2004 |
| WO | WO 2005/037972 A1 | 4/2005 |
| WO | WO 2005/081935 A2 | 9/2005 |
| WO | WO 2006/034239 A1 | 3/2006 |

* cited by examiner

DENTURE FIXATIVE COMPOSITION

CROSS-REFERENCE TO RELATED PATENT APPLICATIONS

This patent application is a continuation-in-part of copending U.S. patent application Ser. No. 11/319,916, filed Dec. 28, 2005, herein incorporated by reference in its entirety.

FIELD OF THE INVENTION

The present invention relates to denture fixative compositions.

BACKGROUND ART

Dentures are removable appliances that serve as a replacement for missing teeth and neighboring structures in the oral cavity. Denture fixative compositions are widely used to hold dentures in place, both while the user's mouth is at rest and particularly during mastication. Such denture fixative compositions should also perform their intended function without causing irritation to the mucosal denture surfaces. Ideal denture fixative compositions make the users of dentures confident that their dentures will remain fixed in place while functioning as intended. This is sometimes difficult to achieve particularly where dentures are not fitted perfectly or where the denture fit deteriorates over time due to denture wear or changes in the mucosal denture surfaces.

Denture fixatives come in many forms including pastes, liquids, powders and aerosols. Denture fixatives may also be supplied as liners or adhesive-like strips. In all cases, it is important that good tack is achieved as soon as the dentures are properly positioned in the mouth. It is also important that the fixatives be capable of being readily spread and distributed across the denture-mucosal interface to produce sufficient adhesion to resist the stresses encountered upon mastication. Finally, the fixatives must perform well under the environmental changes typically encountered in the user's mouth such as the temperature changes experienced in drinking very hot or very cold beverages like tea, coffee or cold iced drinks or eating very hot or very cold foods.

Over the years, there have been numerous improvements in denture fixative compositions. Both synthetic and natural polymers and gums have been used alone or in combination with denture fixative compositions and have been combined with various adhesives and other materials in order to achieve such improvements. For example, denture fixative compositions using alkyl vinyl ether-maleic copolymers and salts and derivatives thereof are known to provide good adhesion. U.S. Pat. No. 3,003,988 to D. P. Germann et al., issued Oct. 10, 1961, describes certain synthetic water-sensitized water-insoluble polymeric materials comprising synthetic, hydrophilic, colloidal materials in the form of mixed partial salts of lower alkyl vinyl ether-maleic anhydride-type copolymers, where the mixed partial salts and esters contain both divalent calcium and monovalent alkali cations. U.S. Pat. No. 4,373,036 to Tiang-Shing Chang et al., issued Feb. 8, 1983, relates to improved denture fixative compositions containing a dentally acceptable excipient and a fixative mixture comprising hydroxypropyl cellulose and at least one partially neutralized alkyl vinyl ether-maleic acid or anhydride copolymer, optionally partly crosslinked, a partially neutralized, optionally partly crosslinked polyacrylic acid, or a precursor combination of copolymer or polyacrylic acid, neutralizing agents, and optionally crosslinked agents or polyethylene oxide. U.S. Pat. No. 5,006,571 to Lori D. Kumar et al, issued Apr. 9, 1991, describes improved denture adhesive base compositions comprising a substantially anhydrous mixture of a mixed Na/Ca salts of methyl vinyl ether-maleic acid, sodium carboxymethyl cellulose and a trivalent cation.

It is therefore an important object of this invention to provide new and improved denture fixative compositions that resist the stresses at the denture-mucosal interface encountered upon mastication.

It is a further object of the present invention to provide denture fixative compositions that work well immediately after application and retain their fixative properties for prolonged periods of time.

Yet another object of the present invention is to provide denture fixative compositions that perform well in spite of the extreme environmental changes typically encountered in the user's mouth.

Still another object of the present invention is to provide denture fixative compositions that do not cause oral mucosal irritation and further may be used to protect select areas of the gums or other oral surfaces.

These and other objects of the invention will become apparent to those skilled in the art from the following detailed description of the invention.

BRIEF SUMMARY OF THE INVENTION

This invention relates to denture fixative compositions that can be formulated and used in the form of pastes, liquids, powders, aerosols, etc., or in making adherent layers of liners and adhesive-like strips used as denture fixatives. Among these, the paste denture fixative compositions are preferred.

In the practice of the invention, required ingredients taken from each of the three distinct categories described below are combined with adjunct ingredients including conventional vehicles, emollients, flavorants, colorants, preservatives, therapeutic components, etc. to form unique unexpectedly effective denture fixative compositions. The required ingredients include:

a. at least one copolymer selected from the group consisting of lower alkyl vinyl ether-maleic anhydride copolymer and derivative thereof;

b. at least one water-insoluble and water-swelling polymer; and c. at least one additional adhesive material selected from the group consisting of natural gums, synthetic polymeric gums, karaya gum, guar gum, gelatin, algin, sodium alginate, tragacanth, chitosan, polyethylene glycol, acrylamide polymers, carboxyvinyl polymer, polyvinyl alcohol, polyvinylpyrrolidone, cellulose derivatives and mixtures thereof.

The present composition does not cause oral mucosal irritation and may also be used to protect oral mucosal surfaces. For example, it may be coated onto canker sores to protect those areas from irritation while healing proceeds.

DETAILED DESCRIPTION OF THE INVENTION

The present invention is a denture fixative composition comprising a combination of ingredients from three distinct categories that can be used in the form of pastes, liquids, powders and aerosols or in the adherent layers of liners and adhesive-like strips used as denture fixatives. Among these, the paste denture fixatives are preferred and mainly illustrated in the formulations and examples described below.

A denture fixative composition comprising a combination of these three ingredients resists the stresses at the denture-mucosal interface encountered upon mastication. This combination also works well immediately after application and retains its fixative properties for prolonged periods of time. Additionally, denture fixative compositions with these three ingredients perform well under the environmental changes typically encountered in the user's mouth.

The three categories of ingredients that make up the fixative composition are:
  a. at least one copolymer selected from the group consisting of lower alkyl vinyl ether-maleic anhydride copolymer and derivative thereof;
  b. at least one water-insoluble and water-swelling polymer; and
  c. at least one additional adhesive material.

Ingredient a: Lower Alkyl Vinyl Ether-Maleic Anhydrides Copolymer and Derivatives Thereof The lower alkyl vinyl ether-maleic anhydride copolymer and derivative thereof useful in the invention dissolve slowly in the mouth and contribute adhesive properties as they take up water. These lower alkyl vinyl ether-maleic acid polymers may be obtained by polymerizing a lower alkyl vinyl ether monomer, such as methyl vinyl ether, ethyl vinyl ether, divinyl ether, propyl vinyl ether and isobutyl vinyl ether, with maleic anhydride to yield the corresponding lower alkyl vinyl ether-maleic anhydride polymer which is readily hydrolyzable to the acid polymer. "lower alkyl" in the copolymer includes C1-C8 alkyl, preferably C1-C6 alkyl, and yet more preferably C1-C4 alkyl. Salt forms of the copolymers are also commercially available and can be used. For example, salt forms of the copolymers may be used in which the cationic ion is a monovalent, bivalent, or trivalent cation. Also, combinations of such salts may be used. Sodium and calcium forms of the copolymer salts and mixtures of such salt forms may be used.

For example, International Specialty Products of Wayne, N.J., USA provides GANTREZ MS-955 salt, which is particularly suitable in the practice of this invention. This copolymer has both sodium and calcium salts in one molecule and is supplied as a powder. The copolymer is slowly soluble in water resulting in amber-colored solutions with high viscosity and adhesion. The divalent calcium ion lightly crosslinks the material through ion bridges to reduce its solubility and increase its cohesive strength and viscoelasticity. It is believed that the repeating units may be represented as:

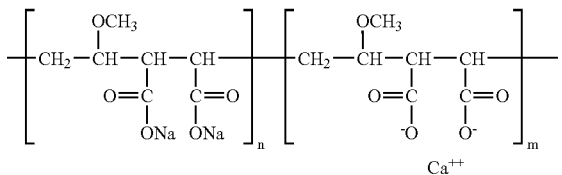

The approximate weight average molecular weight of GANTREZ MS-955 is 1,000,000 and its Brookfield viscosity (mPa·S (11.1% solids aq.)) is 700-3000. The lower alkyl vinyl ether-maleic anhydride copolymer and derivative thereof with a weight average molecular weight of about 200,000 to 2,000,000 is preferably used.

At least one copolymer selected from the group consisting of lower alkyl vinyl ether-maleic anhydride copolymer and derivative thereof should comprise from about 10 to about 55%, preferably from about 20 to about 40%, and yet more preferably from about 27 to about 31% by weight of the dental fixative composition.

Ingredient b: Water-Insoluble and Water-Swelling Polymers

Of the above three ingredients, a denture fixative composition containing ingredients a and c is already known. However, no dental fixative composition containing ingredient b together with ingredients a and c has been reported yet. When the appropriate levels of water-insoluble and water-swelling polymers along with ingredients from the other two categories are used unexpectedly effective denture fixative compositions are obtained.

These polymers must be water-insoluble at ambient temperatures and preferably will be water-insoluble at temperatures below about 60° C. Useful water-insoluble and water-swelling polymers include low-substituted hydroxypropyl cellulose, croscarmellose sodium, calcium carboxymethyl cellulose, agar and mixtures thereof. We refer to the low-substituted hydroxypropyl cellulose below as L-HPC.

L-HPC, agar, and croscarmellose sodium are preferable as water-insoluble and water-swelling polymers. L-HPC is more preferable, and the combined use of L-HPC and agar is particularly preferable. The use of L-HPC is advantageous in view of increasing the maximum adhesiveness. When adjunct ingredients such as flavorants, preservatives, etc., are added to a denture fixative composition, the maximum adhesiveness and adhesiveness over time may tend to decrease. The combined use of L-HPC and agar can suppress this decrease of adhesiveness and maintain high adhesiveness over time.

When L-HPC and agar are used in combination, the blending weight ratio of L-HPC to agar is preferably 2.5 or less, and more preferably in the range of 0.5 to 1.5.

Low-Substituted Hydroxypropyl Cellulose (L-HPC)

Low-substituted hydroxypropyl cellulose (which may includes "cellulose 2-hydroxypropyl ether (low-substituted)" (CAS 9004-64-2) which has the structural formula:

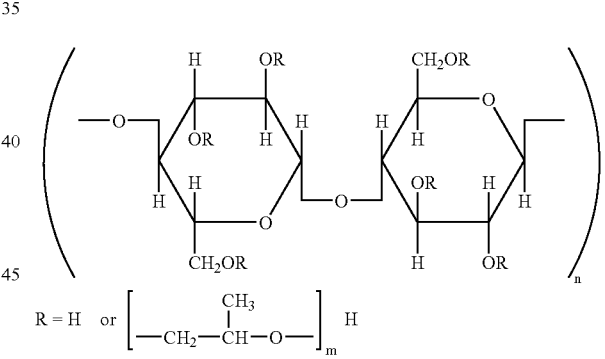

wherein m is an integer of 1 or more.

L-HPC is a low-substituted hydroxypropyl ether of cellulose in which a small proportion of the three hydroxyl groups contained in the β-o-glucopyranosyl ring of the cellulose is etherified with propylene oxide. The number of moles of propylene oxide added to cellulose is smaller in L-HPC than that in hydroxypropyl cellulose (HPC). L-HPC differs from HPC in terms of physical properties. When dried at 105° C. for 1 hour, L-HPC contains not less than 5.0% and not more than 16.0% of hydroxypropoxy groups (—OCH$_2$CHOHCH$_3$). L-HPC does not dissolve in water, rather it swells when wetted. The number of moles of substitution per glucose residue of L-HPC is 0.11 to 0.39. In contrast, the number of moles of substitution per glucose residue of HPC is 2.0 to 4.2.

Modifications of the substituent content and particle size of L-HPC cause changes in the binding characteristics as a result of subtle changes in physical properties. Therefore, the choice of the L-HPC used is of great importance. In the practice of the present invention, it has been found that the choice of L-HPC with the following properties is preferable:

Hydroxypropyl content: about 5.0 to about 16.0% and preferably about 10.0 to about 12.9% by weight.

Particle size: under about 200 microns and preferably under about 100 microns, more preferably from about 20 to about 60 microns.

When the particle diameter is within the above-mentioned range, the composition swells rapidly in the oral cavity. Low-substituted hydroxypropyl cellulose is described in detail on pages C-3262 to C-3265 of Handbook for Japanese Pharmacopoeia, 15$^{th}$ Edition, which is incorporated herein by reference. The hydroxypropoxy group content can be determined according to the method described therein.

Preferred L-HPC includes LH-21, LH-31 and LH-B1 available from Shin-Etsu Chemical Co., Ltd., Tokyo, Japan. More preferred L-HPC includes LH-31. Combinations of these preferred L-HPC ingredients or of any of the noted water-insoluble and water-swelling polymers can be used.

Other water-insoluble and water-swelling polymers that may be used in the practice of the present invention include croscarmellose sodium, calcium carboxymethyl cellulose and agar, as described below.

Croscarmellose Sodium

Croscarmellose sodium, which may also be referred to by the chemical name, cellulose, carboxymethyl ether, sodium salt, crosslinked (CAS 74811-65-7), is insoluble in water, although it swells to 4-8 times its original volume on contact with water. Crosscarmellose sodium is commercially available under the trademark of Ac-Di-Sol (FMC BioPolymer, Newark, Del., USA), Primellose (DMV International GmbH, Veghel, The Netherlands) and Kiccolate (Asahi Kasei Chemicals Corp. Tokyo, Japan).

Calcium Carboxymethyl Cellulose

Calcium carboxymethyl cellulose, which may also referred to by the chemical name, cellulose, carboxymethyl ether, calcium salt (CAS 9050-04-8), is insoluble in water, but swells to twice its volume on contact with water to form suspension. Calcium carboxymethyl cellulose is commercially available under the trademark of ECG 505 (Nichirin Chemical Industries Ltd., Hyogo, Japan)

Agar

Agar is a biopolymer found in the cell walls of several species of seaweeds, such as *Gelidium amansii, Gracilaria verrucosa, Pterocladia capillacea, Ahnfeltia plicata, Gracilaria gigas*, etc. Agar is thought to have structural functionality, as well as ion exchange and membrane dialysis functionality.

Agar is a biopolymer found in the cell walls of seaweed, and is thought to have a structural functionality, as well as ion exchange and membrane dialysis functionality. Agar is a mixture of a neutral dominating polysaccharide called "agarose" and a charged polymer called "agaropectin". The agarose skeleton contains as a basic unit agarobiose or neo-agarobiose, which are composed of alternating a D-galactopyranose unit and a 3,6-anhydro-L-galactopyranose unit that are bonded to each other in such a manner that the 1-position of D-galactopyranose is beta-bonded to the 4-position of 3,6-anhydro-L-galactopyranose and the 3-position of D-galactopyranose is alpha-bonded to the 1-position of 3,6-anhydro-L-galactopyranose.

The agaropectin has the same repeating units as agarose but approximately every tenth D-galactopyranose subunit occurs a substituted sulfate, methyl, pyruvic or acetyl functional group. Agar is commercially available and easily attainable. Agar has long been used, for example, as a food ingredient and is also currently used in the biochemical industry. Agar is insoluble in cold water, swells, and is soluble in boiling water.

In the present invention, agar with a high molecular weight is preferably used. More specifically, agar with a weight average molecular weight of about 400,000 or higher, more preferably about 400,000 to about 1,000,000, and still more preferably about 700,000 to about 800,000 is desirable. When the molecular weight of the agar used is within this range, the denture fixative composition will have enhanced adhesiveness.

The substituent of 3,6-anhydro-L-galactopyranose in the agar is preferably a sulfuric acid group. When hydroxyl groups of the agar are substituted by sulfuric acid groups, the denture fixative composition will have enhanced hydrophilicity and thus an enhanced swelling property.

Although general agar, which does not completely dissolve unless it is kept in hot water at around 100° C. for about 5 to about 10 minutes, can also be used in the invention, agar that dissolves in water at a relatively low temperature, i.e., highly water-soluble agar, is preferably used. Such highly water-soluble agar dissolves at a temperature lower than around 100° C. For example, it completely dissolves in water at 70 to 90° C. The highly water-soluble agar preferably has a solubility of 70% or higher, more preferably 80% or higher, and still more preferably 90% or higher, at 80° C. in the solubility tests described below. The highly water-soluble agar is commercially available. Examples of highly water-soluble agar usable in the invention include such products as UP-16K, UP-26K UP-37, UP-37K and UZ-5K manufactured by Ina Food Industry Co., Ltd.

In the solubility tests, agar is dispersed in water at a concentration of 1.5 wt % and heated to a desired temperature. After the solution has been maintained for 10 minutes, it is cooled to 10° C. with water until the agar gels, and then the gel strength is measured. The aforementioned solubility is defined as the ratio between the gel strength of the agar heated to the desired temperature and the gel strength of the agar that has been completely dissolved by heating to 100° C. The agar gel strength can be typically measured by the Nikkansui method. In this method, an aqueous solution containing 1.5 wt % agar is first prepared. The solution is then left standing at 20° C. for 15 hours to set the gel. The gel strength is determined, using a rheometer or the like, by measuring the maximum weight that the gel surface can withstand per 1 cm$^2$ for 20 seconds.

Agar is usually prepared by boiling the raw material algae with a small amount of sulfuric acid in water at about 100° C. to obtain a hot water extract in the form of a sol, then cooling to solidify the extract, and drying. Although agar prepared by such an ordinary production process can be used as the agar in the present invention, agar alternatively obtained by a process not containing the step of cooling to solidify, more specifically, a process comprising directly drying a hot water extract in the form of a sol by means of drum drying, spray drying, etc., without solidifying to a gel can also be used. The above-mentioned highly water-soluble agar is obtained typically by this production process. Highly water-soluble agar is preferable because it enhances the swelling properties of denture fixatives at the temperature of use in the oral cavity. Such an alternative production process is disclosed in Examined Patent Publication No. 1988-5053, etc., and this process disclosed in these publications is preferable for producing highly water-soluble agar.

The water-insoluble and water-swelling polymers should comprise from about 1 to about 60%, preferably about 2 to about 30%, and yet more preferably from about 1 to about 13% by weight of the denture adhesive composition. Most preferably, the water-insoluble and water-swelling polymers will comprise about 4 to about 7% by weight of the denture adhesive composition.

The most preferable water-insoluble and water-swelling polymer is obtained by combining L-HPC and agar. A denture fixative composition containing both of these components not only has a high maximum adhesiveness but is also exhibits excellent storage stability. It is believed that the maximum adhesiveness is mainly derived from the L-HPC, and the storage stability is mainly derived from the agar.

Ingredient c: Additional Adhesive Materials

The additional adhesive materials will be chosen from the following: natural gums, synthetic polymeric gums, karaya gum, guar gum, gelatin, algin, sodium alginate, tragacanth, chitosan, polyethylene glycol, acrylamide polymers, carboxyvinyl polymers (e.g., carbopol), polyvinyl alcohol, polyvinylpyrrolidone, cellulose derivatives and mixtures thereof. Alternatively, the additional adhesive materials may be chosen from the following: methyl cellulose, sodium carboxymethyl cellulose, hydroxyethyl cellulose, hydroxypropyl cellulose, hydroxyl propylmethyl cellulose, carboxymethyl cellulose, and mixtures thereof.

Among the above additional adhesive materials, sodium carboxymethyl cellulose is currently preferred. This material is a powder that when moistened becomes hydrated and tacky or gummy thereby providing additional adhesive functionality to the dental adhesive composition. The carboxymethyl cellulose gums are water-soluble, anionic long chain polymers whose properties vary to some extent depending on the number of carboxymethyl groups that are substituted per anhydroglucose unit in each cellulose molecule. Combinations of different water-soluble adhesive polymers can be used.

The additional adhesive materials should comprise from about 1 to about 35%, preferably from about 10 to about 30%, and yet more preferably from about 19 to about 22% by weight of the dental adhesive composition.

Dental fixative creams may include as additional ingredients emollients such as petroleum jelly, mineral oil and other hydrocarbons suitable for use as emollients. The emollients may be present in the fixative composition at a level of from about 10 to about 50% by weight of the composition.

The fixative composition may also include silicon dioxide at a level of about 0.1 to about 9.0% by weight of the composition. It may also include flavorants, colorants, preservatives, and mixtures thereof, as desired.

Finally, the denture fixative composition may include a therapeutic component selected from the group consisting of medically acceptable anti-bacterial agents, anti-fungal agents, anti-inflammatory agents and mixtures thereof.

Figure 1:
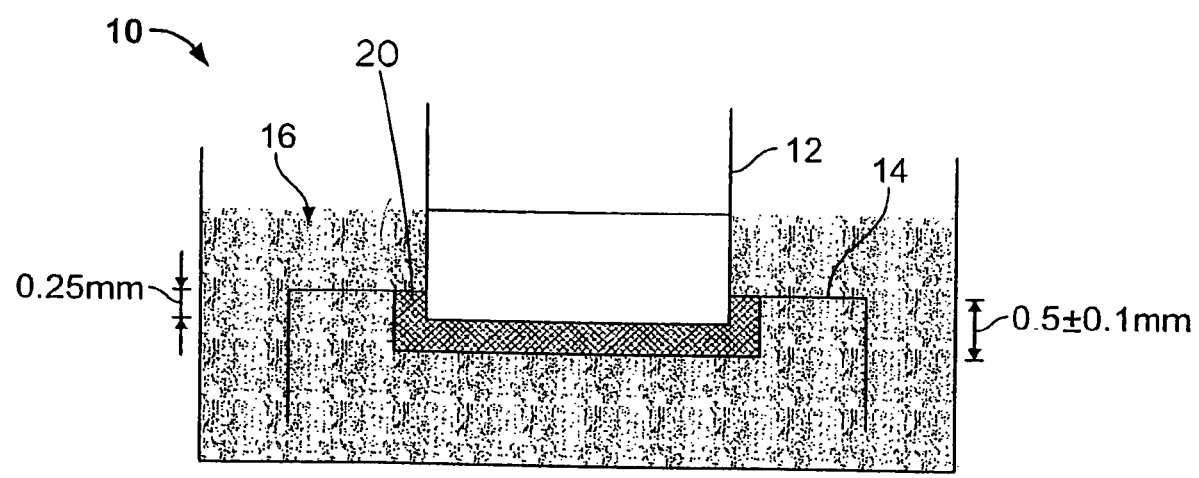
FIG. 1. is a diagrammatic representation of the adhesive strength test apparatus used in Example 2 of the application.
Figure 2:
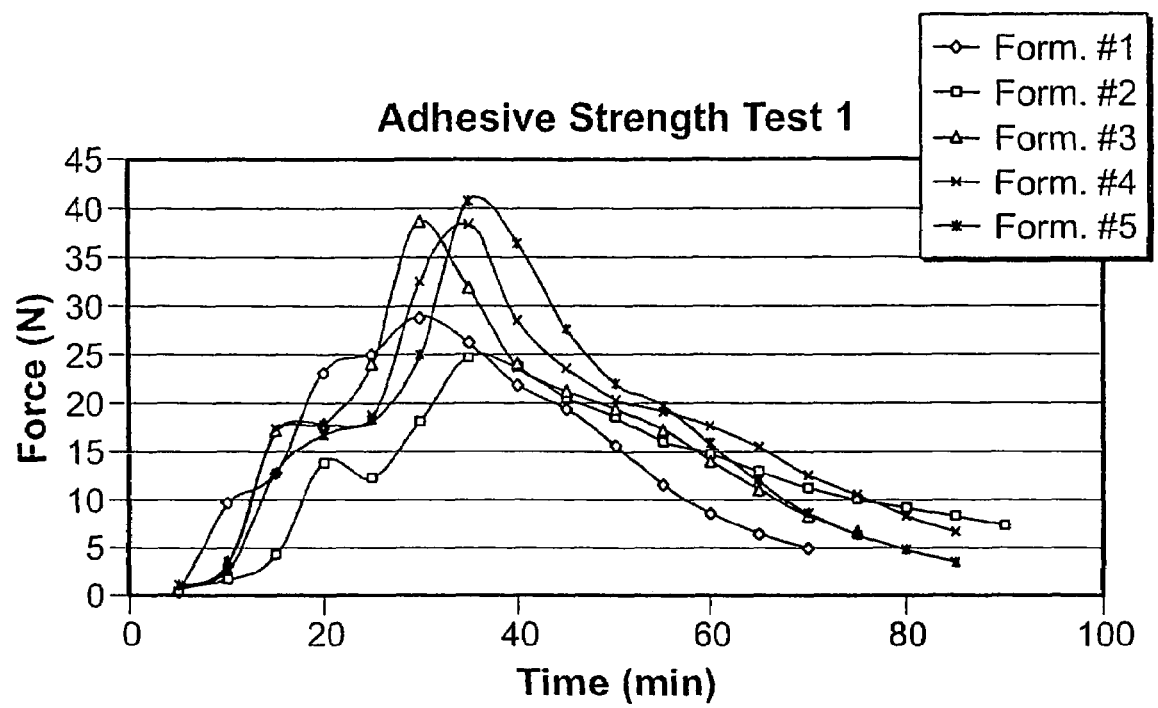
FIG. 2 is a graph comparing the adhesiveness over time of a base formulation free of water-insoluble and water-swelling polymer to three test formulations containing different L-HPC products and a second base formulation containing water soluble hydroxypropyl cellulose.
Figure 3:
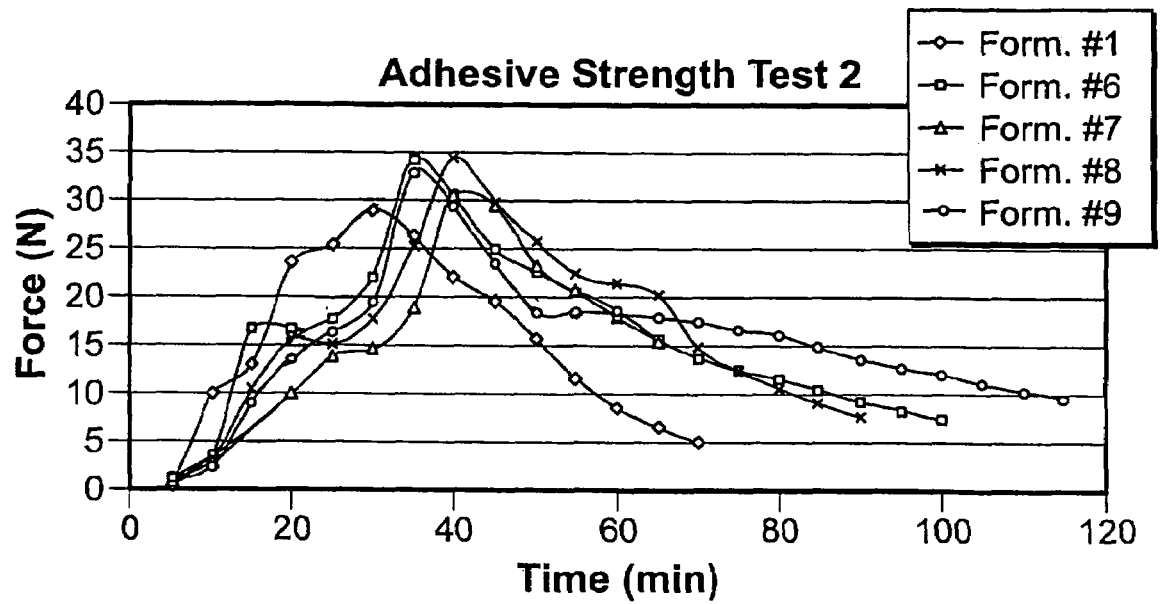
FIG. 3 is a graph providing a comparison of the adhesiveness over time of a base formulation free of water-insoluble and water-swelling polymer to four formulations containing two different croscarmellose sodium and agar.
Figure 4:
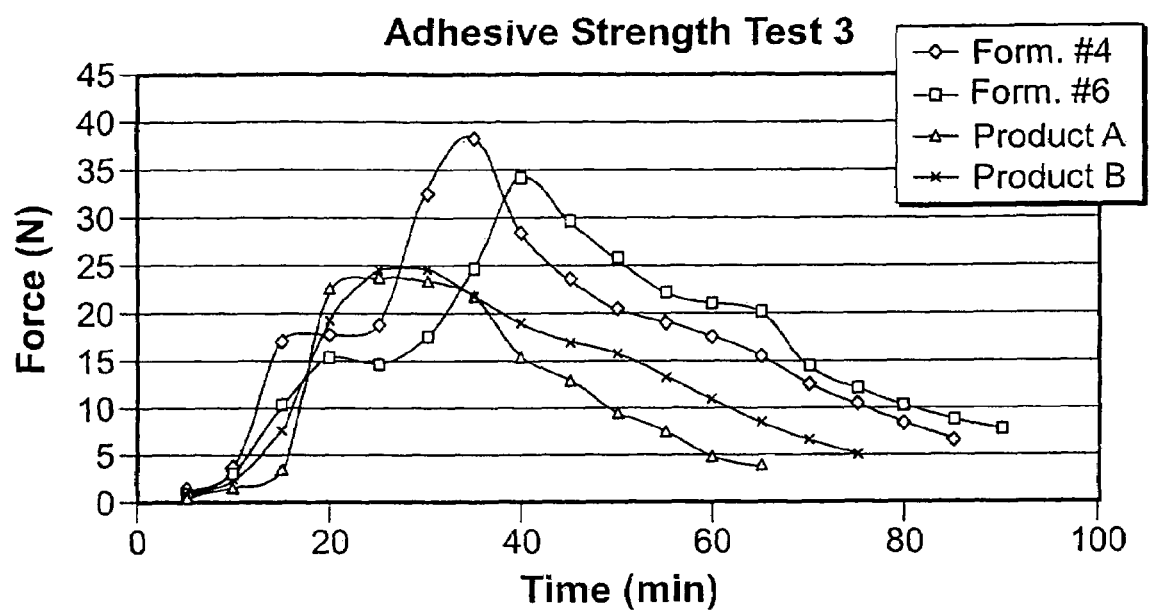
FIG. 4 is a graph in which compositions of the present of invention-containing L-HPC and croscarmellose sodium were compared with the commercially available products.
Figure 5:
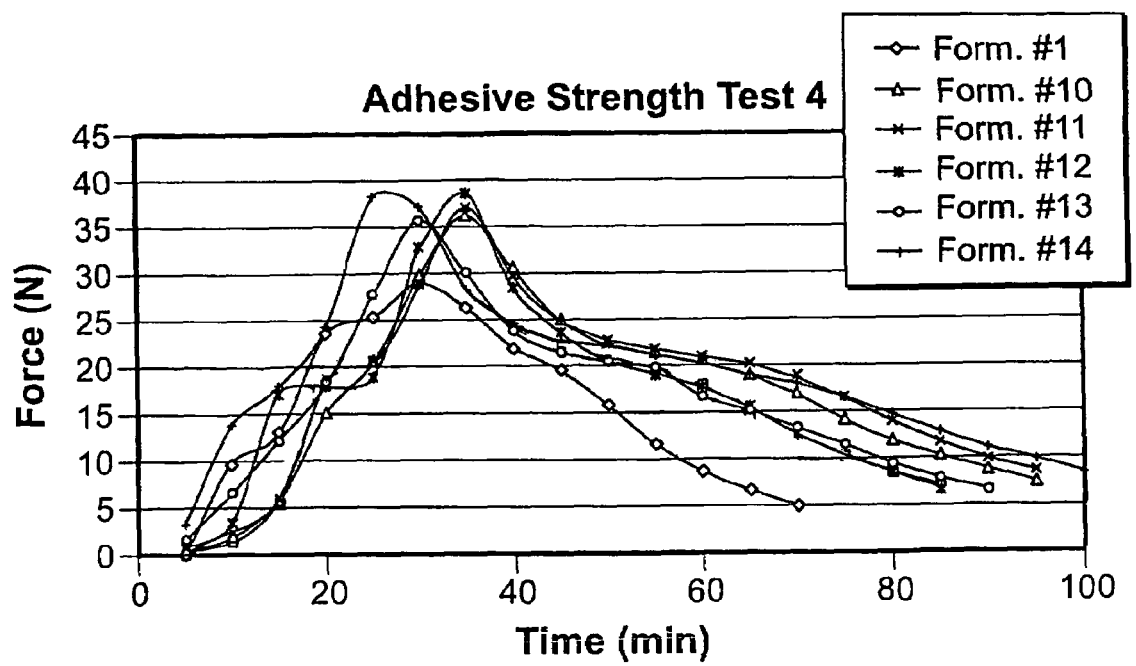
FIG. 5 is a graph of adhesiveness vs. time for a series of test formulations with varying levels of L-HPC.

The following Examples are given to illustrate the present invention, and are not intended to limit the scope of the invention.

The materials used in the Examples are as follows.

Ingredient a
　Gantrez MS-955: salt of methyl vinyl ether-maleic anhydride copolymer (Na/Ca)

Ingredient b
　L-HPC: product of Shin-Etsu Chemical Co., Ltd.; details shown below:

TABLE 1

| | L-HPC | | |
|---|---|---|---|
| Grade | | Average particle diameter | Particle form |
| LH-31 | | 20μ | Fine powder |
| LH-21 | | 40μ | Fiber |
| LH-B1 | | 50μ | Heavy, non-fiber |

Croscarmellose sodium: "Ac-Di-Sol", "Primellose", "Kiccolate"
　Calcium carboxymethyl cellulose: "ECG 505"
　Agar-1: "Yamato" manufactured by Ina Food Industry Co., Ltd., having a weight average molecular weight of 700,000 to 800,000
　Agar-2: "UP-37" manufactured by Ina Food Industry Co., Ltd., having a solubility of 90% or higher at 80° C.

Ingredient c
　Sodium carboxymethyl cellulose
　HPC: product of Sigma-Aldrich, in which the average number of moles of substituents is 3.8 per glucose residue (3.4 to 3.8 in the product specifications)

Other Ingredients
　Mineral oil-1: medium viscosity [viscosity (40° C., ASTM D445) of 65.0/70.0]
　Mineral oil-2: low viscosity [viscosity (40° C., ASTM D445) of 34.9/37.3]
　White petrolatum jelly-1: consistency (ASTM D937) of 195/230
　White petrolatum jelly-2: consistency (ASTM D937) of 180/210
　White petrolatum jelly-3: consistency (ASTM D937) of 210/240
　Silicon dioxide
　Coloring agent: FD&C Color #3
　Flavor
　Preservative: propyl paraben

EXAMPLE 1

As shown in Tables 2 to 4 below, paste-form denture fixative compositions that contained ingredients a and c but did not contain ingredient b (Formulations #1 and #2; comparative examples) and paste-form denture fixative compositions containing ingredients a, b and c (Formulations #3 to #14; present invention) were prepared in a standard manner, and the adhesive strength of these formulations was measured. The unit for the numbers in the tables is wt. %. The adhesive strength of commercially available denture fixative compositions A and B shown in Table 5 below was also measured in addition to the formulations of Tables 2 to 4 above. FIGS. 2 to 5 show the measurement results.

TABLE 2

| Experimental Composition | Formulation No. | | | | |
|---|---|---|---|---|---|
| Components | #1 | #2 | #3 | #4 | #5 |
| Gantrez MS-955 | 31.5 | 29.5 | 29.5 | 29.5 | 29.5 |
| Sodium carboxymethyl cellulose | 22.0 | 20.5 | 20.5 | 20.5 | 20.5 |
| Mineral Oil-1 | 24.0 | 22.5 | 22.5 | 22.5 | 22.5 |
| White petroleum jelly-1 | 22.0 | 20.5 | 20.5 | 20.5 | 20.5 |
| Silicon dioxide | 0.5 | 0.5 | 0.5 | 0.5 | 0.5 |
| Hydroxypropyl cellulose (Avg. Mw. 100,000) | | 6.5 | | | |
| L-HPC (LH-21) | | | 6.5 | | |
| L-HPC (LH-31) | | | | 6.5 | |
| L-HPC (LH-B1) | | | | | 6.5 |
| Total | 100 | 100 | 100 | 100 | 100 |
| Maximum adhesive strength (N) | 29.0 | 24.8 | 38.8 | 38.5 | 41.2 |

TABLE 3

| Experimental Composition | Formulation No. | | | |
|---|---|---|---|---|
| Components | #6 | #7 | #8 | #9 |
| Gantrez MS-955 | 29.5 | 29.5 | 29.5 | 29.5 |
| Sodium carboxymethyl cellulose | 20.5 | 20.5 | 20.5 | 20.5 |
| Mineral Oil-1 | 22.5 | 22.5 | 22.5 | 22.5 |
| White petroleum jelly-1 | 20.5 | 20.5 | 20.5 | 20.5 |
| Silicon dioxide | 0.5 | 0.5 | 0.5 | 0.5 |
| Croscarmellose sodium (Ac-Di-Sol) | 6.5 | | | |
| Croscarmellose sodium (Primellose) | | 6.5 | | |
| Croscarmellose sodium (Kiccloate) | | | 6.5 | |
| Agar-1 | | | | 6.5 |
| Total | 100 | 100 | 100 | 100 |
| Maximum adhesive strength (N) | 34.5 | 30.4 | 34.6 | 33.0 |

TABLE 4

| Experimental Composition | Formulation No. | | | | |
|---|---|---|---|---|---|
| Components | #10 | #11 | #12 | #13 | #14 |
| Gantrez MS-955 | 30.54 | 30.00 | 29.50 | 28.64 | 27.39 |
| Sodium carboxymethyl cellulose | 21.34 | 20.95 | 20.50 | 20.02 | 19.12 |
| Mineral Oil-1 | 23.28 | 22.85 | 22.50 | 21.82 | 20.87 |
| White petroleum jelly-1 | 21.34 | 20.95 | 20.50 | 20.02 | 19.12 |
| Silicon dioxide | 0.50 | 0.50 | 0.50 | 0.50 | 0.50 |
| L-HPC (LH-31) | 3.00 | 4.75 | 6.50 | 9.00 | 13.00 |
| Total | 100 | 100 | 100 | 100 | 100 |
| Maximum adhesive strength (N) | 36.1 | 38.0 | 38.5 | 35.7 | 38.2 |

TABLE 5

| Product | Commercially-Available Composition | Maximum adhesive strength (N) |
|---|---|---|
| A | Fixodent Original (P &G) | 23.9 |
| B | Super Polygrip Original (GSK) | 24.9 |

The adhesive strength of Formulations #1-14 was evaluated using a Tinius Olsen multipurpose test stand 10 with an upper rod 12 and lower sample plate 14 arranged as illustrated in FIG. 1. The rod and sample plate were suspended as shown in a water bath 16 maintained at a temperature of about 37° C. Both the rod and the sample plate were made of polymethyl methacrylate, which is a common denture base material. The diameter of the rod was 20±0.5 mm. The circular lower sample plate had a holding area 20 about 22±1 mm in diameter and a depth of 0.5±0.1 mm.

The adhesive strength of the samples was measured by:

a. first filling the holding area with the test composition with any excess material being removed.

b. Both the upper rod and the filled lower plate were then attached to the Tinius Olsen multipurpose test stand.

c. The upper rod was advanced to a depth of 0.25 mm below the surface of the test material in the lower sample plate.

d. The filled lower sample plate with the penetrating rod was placed in the 37° C. water bath to soak the entire sample area.

e. At the end of about five minutes, the upper rod was withdrawn from the sample of a rate of 0.5 mm per minute. A first adhesive force was registered by the Tinius Olsen gauge and recorded.

f. Immediately following the recordal of Tinius Olsen gauge reading, the upper rod was placed in the same position at a depth of 0.25 mm below the surface of the test material in the lower sample plate, while the sample was continuously hydrated.

g. The penetration and decompression (pulling) and associated Tinius Olsen gauge readings were taken until the readings approached zero force.

h. The readings of the entire cycle were recorded and plotted graphically in FIGS. 2-5.

EXAMPLE 2

As shown in Table 6 below, Formulations #L1 to #L4 containing various proportions of L-HPC, and Formulation #1 used in Example 1, were prepared, and the adhesive strength of these formulations was measured by following the procedure in Example 1. Table 6 shows the measured maximum adhesive strength. The maximum adhesive strength of Formulation #1 is 29.0 N.

TABLE 6

| Experimental Composition Components | Formulation No. | | | |
|---|---|---|---|---|
| | #L1 | #L2 | #L3 | #L4 |
| Gantrez MS-955 | 30.54 | 29.14 | 28.64 | 27.39 |
| Sodium carboxymethyl cellulose | 21.34 | 20.34 | 20.02 | 19.12 |
| Mineral Oil-1 | 23.28 | 22.18 | 21.82 | 20.87 |
| White petroleum jelly-1 | 21.34 | 20.34 | 20.02 | 19.12 |

TABLE 6-continued

| Experimental Composition Components | Formulation No. | | | |
|---|---|---|---|---|
| | #L1 | #L2 | #L3 | #L4 |
| Silicon dioxide | 0.50 | 0.50 | 0.50 | 0.50 |
| L-HPC (LH-31) | 3.00 | 6.50 | 9.00 | 13.00 |
| Total | 100 | 100 | 100 | 100 |
| Maximum adhesive strength (N) | 36.1 | 38.5 | 35.7 | 38.2 |

The maximum adhesive strength of Formulations #L1 to #L4, which contains L-HPC, are clearly higher than that of Formulation #1.

EXAMPLE 3

As shown in Table 7 below, Formulations #A1 to #A5 containing various proportions of agar and Formulation #1 used in Example 1 were prepared, and the adhesive strength of these formulations was measured by following the procedure in Example 1. Table 7 shows the measured maximum adhesive strength. The maximum adhesive strength of Formulation #1 is 29.0 N.

TABLE 7

| Experimental Composition Components | Formulation No. | | | | |
|---|---|---|---|---|---|
| | #A1 | #A2 | #A3 | #A4 | #A5 |
| Gantrez MS-955 | 30.54 | 29.50 | 29.14 | 28.64 | 27.39 |
| Sodium carboxymethyl cellulose | 21.34 | 20.50 | 20.34 | 20.02 | 19.12 |
| Mineral Oil-1 | 23.28 | 22.50 | 22.18 | 21.82 | 20.87 |
| White petroleum jelly-1 | 21.34 | 20.50 | 20.34 | 20.02 | 19.12 |
| Silicon dioxide | 0.50 | 0.50 | 0.50 | 0.50 | 0.50 |
| Agar | 3.00 | 6.50 | 7.50 | 9.00 | 13.00 |
| Total | 100 | 100 | 100 | 100 | 100 |
| Maximum adhesive strength (N) | 33.7 | 32.8 | 35.2 | 30.8 | 32.0 |

EXAMPLE 4

As shown in Table 8, Formulations #LA1 to #LA3 containing various proportions of L-HPC and various proportions of agar and Formulation #1 used in Example 1 were prepared, and the adhesive strength of these formulations was measured by following the procedure in Example 1. Table 8 shows the measured maximum adhesive strength. The maximum adhesive strength of Formulation #1 is 29.0 N.

Further, about 30 g each of the formulations was packed into the tubes described below and stored for days to evaluate the ease of squeezing out the formulations. The evaluation was conducted by holding each tube in the right hand, and pressing the tube between the thumb and forefinger of the right hand to squeeze the formulation out of the tube. The evaluation scale is given below. Table 8 shows the evaluation results.

TABLE 8

| Experimental Composition Components | Formulation No. | | |
|---|---|---|---|
| | #LA1 | #LA2 | #LA3 |
| Gantrez MS-955 | 30.00 | 29.00 | 28.50 |
| Sodium carboxymethyl cellulose | 20.75 | 20.25 | 19.75 |
| Mineral Oil-1 | 22.00 | 22.00 | 21.50 |
| White petroleum jelly-1 | 20.75 | 20.25 | 19.75 |
| Silicon dioxide | 0.50 | 0.50 | 0.50 |
| L-HPC (LH-31) | 2.50 | 4.50 | 6.50 |
| Agar-1 | 3.00 | 3.00 | 3.00 |
| FD &C Color #3 | 0.05 | 0.05 | 0.05 |
| Flavor | 0.40 | 0.40 | 0.40 |
| Preservative (propyl paraben) | 0.05 | 0.05 | 0.05 |
| Total | 100 | 100 | 100 |
| Maximum adhesion strength (N) | 31.8 | 31.9 | 37.6 |
| Squeezing ease | A | A | A |

<Evaluation of squeezing ease>
Tubes used: Product of Cebal Americas
Tube diameter: 0.75 in.
Tube length: 3.5 in.
Tube outlet-diameter: 0.172 in.
Amount of formulation in each tube: about 30 g
Test temperature: room temperature (about 20 to 25°C)
Evaluation scale:
 A/easily squeezed out with little force
 B/easily squeezed out with moderate force
 C/required considerable force to squeeze out.
 D/difficult to squeeze out (solidified)

Formulations #LA1 to #LA3 contained a coloring agent, flavor and preservative, in addition to L-HPC and agar. Therefore, these formulations are likely to have lower maximum adhesive strength than Formulation #1. Formulations #LA1 to #LA3 nevertheless showed a considerably higher maximum adhesive strength than Formulation #1. Further, despite the high maximum adhesive strength, Formulations #LA1 to #LA3 were unlikely to solidify and exhibited excellent storage stability as a product.

EXAMPLE 5

As shown in Table 9 below, paste-form denture compositions (Formulations #LA4 to #LA7) were prepared by following the procedure in Example 1 and varying the ingredients.

TABLE 9

| Experimental Composition Components | Formulation No. | | | |
|---|---|---|---|---|
| | #LA4 | #LA5 | #LA6 | #LA7 |
| Gantrez MS-955 | 28.52 | 28.52 | 28.52 | 28.52 |
| Sodium carboxymethyl cellulose | 19.75 | 19.75 | 19.75 | 19.75 |
| Mineral Oil-1 (Moderate viscosity) | | 21.50 | 21.50 | 21.50 |
| Mineral Oil-2 (Low viscosity) | 21.50 | | | |
| White petroleum jelly-1 | | | 19.75 | |
| White petroleum jelly-2 | | 19.75 | | 19.75 |
| White petroleum jelly-3 | 19.75 | | | |
| Silicon dioxide | 0.50 | 0.50 | 0.50 | 0.50 |
| L-HPC (LH-31) | 6.50 | 6.50 | | 6.50 |
| L-HPC (LH-B1) | | | 6.50 | |
| Agar-1 | 3.00 | 3.00 | 3.00 | |
| Agar-2 | | | | 3.00 |
| FD &C Color #3 | 0.03 | 0.03 | 0.03 | 0.03 |

TABLE 9-continued

| Experimental Composition | Formulation No. | | | |
|---|---|---|---|---|
| Components | #LA4 | #LA5 | #LA6 | #LA7 |
| Flavor | 0.40 | 0.40 | 0.40 | 0.40 |
| Preservative (propyl paraben) | 0.05 | 0.05 | 0.05 | 0.05 |
| Total | 100 | 100 | 100 | 100 |

EXAMPLE 6

The maximum adhesive strength of paste-form denture fixatives including Products A and B mentioned above were measured by following the procedure of Example 1. Table 10 shows the results. Table 10 also shows, for comparison, the maximum adhesive strength of Formulation #1 and Formulations #L2 (containing 6.5% L-HPC), #A2 (containing 6.5% agar) and #LA3 (containing 6.5% L-HPC and 3% agar) according to the present invention.

TABLE 10

| Formulation No. or Product | Maximum adhesion strength (N) |
|---|---|
| #1 | 29.0 |
| #L2 | 38.5 |
| #A2 | 32.8 |
| #LA3 | 37.6 |
| A | 23.9 |
| B | 24.9 |
| C | 24.4 |
| D | 17.5 |
| E | 26.4 |
| F | 24.3 |
| G | 21.0 |
| H | 17.2 |

EXAMPLE 7

Denture-fixative compositions were prepared in a standard manner using Formulations #PO1 to #PO3 (powdery denture fixatives shown in Tables 11 and 12 below), Formulation #PA1 (paste-form denture fixative), and Formulations #GO1 to #G03 (granular denture fixatives).

TABLE 11

| Experimental Composition | Formulation No. | | | |
|---|---|---|---|---|
| Components | #PO1 | #PO2 | #PO3 | #PA1 |
| Gantrez MS-955 | 40.0 | 40.0 | 40.0 | 29.5 |
| Sodium carboxymethyl cellulose | 52.5 | 52.5 | 52.5 | 20.5 |
| L-HPC (LH-31) | 6.5 | | 4.5 | |
| Agar-1 | | 6.5 | 2.0 | |
| Calcium carboxymethyl cellulose (ECG505) | | | | 6.5 |
| Mineral Oil-1 | | | | 22.5 |
| White petroleum jelly-1 | | | | 20.5 |
| Silicon dioxide | | | | 0.5 |
| Flavor | 1.0 | 1.0 | 1.0 | |
| Total | 100 | 100 | 100 | 100 |

TABLE 12

| Experimental Composition | Formulation No. | | |
|---|---|---|---|
| Components | #G1 | #G2 | #G3 |
| Gantrez MS-955 | 35.0 | 35.0 | 35.0 |
| Sodium carboxymethyl cellulose | 46.5 | 46.5 | 46.5 |
| L-HPC (LH-31) | 6.5 | | 4.5 |
| Agar-1 | | 6.5 | 2.0 |
| White petroleum jelly-1 | 11.0 | 11.0 | 11.0 |
| Flavor | 1.0 | 1.0 | 1.0 |
| Total | 100 | 100 | 100 |

We turn now to a discussion of the test results as reflected in FIGS. 2-5.

FIG. 2

This Figure provides a comparison of the adhesiveness over time of a base composition (Formulation #1) free of water-insoluble and water-swelling polymer to test compositions using three different L-HPC products (Formulations #3, #4 and #5) and a second base formulation containing water soluble hydroxypropyl cellulose (Formulation #2) as a reference. As can be seen from the graph of adhesive force vs. time of this Figure, the formulations containing L-HPC generally have markedly higher adhesiveness overall and the superior adhesiveness is maintained over time.

FIG. 3

The graph in this Figure provides a comparison of the adhesiveness over time of a base composition (Formulation #1) free of water-insoluble and water-swelling polymer to five test compositions-containing different croscarmellose sodium products (Formulations #6, #7 and #8), and agar (Formulation #9). As can be seen from the graph of adhesive force vs. time of this Figure, the formulations containing croscarmellose sodium and agar generally have better maximum adhesiveness and comparable adhesiveness over time to the base formulation free of water-insoluble and water-swelling polymer.

FIG. 4

In this Figure, compositions of the present of invention containing L-HPC (Formulation #4) and croscarmellose sodium (Formulation #6) were compared with the commercially available compositions, Product-A and Product-B. The results obtained demonstrate that the compositions of the present invention have substantially greater maximum adhesiveness than any of the commercial products tested and also superior adhesiveness over time as compared to Product-A and Product-B.

FIG. 5

The graph in this Figure reports adhesiveness vs. time for a series of test formulations with varying levels of L-HPC. The test results show generally substantially superior adhesiveness for all of the formulations containing insoluble swelling polymers, in comparison to formulations without insoluble swelling polymers. Additionally, Formulation #14 showed superior early adhesiveness, Formulations #12 showed superior maximum adhesiveness, and all of the formulations containing L-HPC showed superior adhesiveness over time in comparison to the formulation free of water-insoluble and water-swelling polymer.

If desired, denture fixatives in the forms of liquids, powders, aerosols, and even liners or adhesive-like strips may be formulated using compositions as set forth above, substituting appropriate types and levels of the adjunct ingredients required to formulate such compositions. The identity and appropriate levels of these ingredients are well-recognized by those skilled in the art.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A denture fixative composition comprising:
   a. at least one copolymer selected from the group consisting of lower alkyl vinyl ether-maleic anhydride copolymer and salt derivative thereof;
   b. at least one water-insoluble and water-swelling polysaccharide selected from the group consisting of low-substituted hydroxypropyl cellulose having a hydroxypropyl content of 5.0 to 16.0%, agar having a weight average molecular weight of 400,000 or more and mixtures thereof; and
   c. at least one additional adhesive material selected from the group consisting of natural gums, synthetic polymeric gums, karaya gum, guar gum, gelatin, algin, sodium alginate, tragacanth, chitosan, polyethylene glycol, acrylamide polymers, carboxyvinyl polymer, polyvinyl alcohol, polyvinylpyrrolidone, water-soluble cellulose derivatives and mixtures thereof.

2. The denture fixative composition of claim 1 wherein the water-insoluble and water-swelling polymer is present at a level from about 1 to about 60% by weight of the denture fixative composition.

3. The denture fixative composition of claim 1 wherein the additional adhesive material is at least one water-soluble cellulose derivative selected from the group consisting of methyl cellulose, sodium carboxymethyl cellulose, hydroxyethyl cellulose, hydroxypropyl cellulose, hydroxypropyl methyl cellulose, carboxymethyl cellulose, and mixtures thereof.

4. The denture fixative composition of claim 1 wherein the additional adhesive material is sodium carboxymethyl cellulose.

5. The denture fixative composition of claim 1 where in the additional adhesive material is present at a level of from about 1 to about 35% by weight of the denture fixative composition.

6. The denture fixative composition of claim 1 wherein the water-insoluble and water-swelling polymer is water-insoluble at ambient temperature.

7. The denture fixative composition of claim 1 wherein the water-insoluble and water-swelling polymer has a particle size under about 200 microns.

8. The denture fixative composition of claim 1 wherein the water-insoluble and water-swelling polymer is low-substituted hydroxypropyl cellulose.

9. The denture fixative composition of claim 8 wherein the water-insoluble and water-swelling polymer is a low-substituted hydroxypropyl cellulose having a hydroxypropyl content of about 10.0 to about 12.9%.

10. The denture fixative composition of claim 1 wherein the water-insoluble and water-swelling polymer is agar.

11. The denture fixative composition of claim 10 wherein the water-insoluble and water-swelling polymer is agar having a weight average molecular weight from about 700,000 to about 800,000.

12. The denture fixative composition of claim 10 wherein the water-insoluble and water-swelling polymer is an agar whose solubility measured by dissolving the agar at a concentration of 1.5 wt. % in 80° C. water is 70% or more.

13. The denture fixative composition of claim 1 wherein the water-insoluble and water-swelling polymer is present at a level of from about 1 to about 30% by weight of the denture fixative composition.

14. The denture fixative composition of claim 1 wherein the lower alkyl vinyl ether-maleic anhydride copolymer or a derivative comprises at least one cationic ion selected from the group consisting of monovalent, bivalent, trivalent cations and mixtures thereof.

15. The denture fixative composition of claim 14 wherein the cationic ion is at least one ion selected from the group consisting of calcium, sodium, and mixtures thereof.

16. The denture fixative composition of claim 1 wherein the lower alkyl vinyl ether-maleic anhydride copolymer or a derivative thereof is present at a level of from about 10 to about 55% by weight of the denture fixative composition.

17. The denture fixative composition of claim 1 further including an emollient at a level of from about 10 to about 50% by weight of the denture fixative composition.

18. The denture fixative composition of claim 17 wherein the emollient is at least one material selected from the group consisting of petroleum jelly, mineral oil, and mixtures thereof.

19. The denture fixative composition of claim 1 further including silicon dioxide at a level of from about 0.1 to about 9% by weight of the denture fixative composition.

20. The denture fixative composition of claim 1 further including at least one component selected from the group consisting of flavorants, colorants, preservatives, and mixtures thereof.

21. The denture fixative composition of claim 1 further including at least one therapeutic component selected from the group consisting of medically acceptable anti-bacterial agents, anti-fungal agents, anti-inflammatory agents and mixtures thereof.

* * * * *